United States Patent
Derkx et al.

(10) Patent No.: US 11,723,555 B2
(45) Date of Patent: Aug. 15, 2023

(54) SYSTEMS AND METHODS FOR SUPPRESSING PEAKS IN A SEISMOCARDIOGRAM

(71) Applicant: KONINKLIJKE PHILIPS N.V., Eindhoven (NL)

(72) Inventors: Rene Martinus Maria Derkx, Eindhoven (NL); Thomas Gerhard Emmrich, Gaertringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 553 days.

(21) Appl. No.: 16/617,468

(22) PCT Filed: May 18, 2018

(86) PCT No.: PCT/EP2018/063095
§ 371 (c)(1),
(2) Date: Nov. 26, 2019

(87) PCT Pub. No.: WO2018/219692
PCT Pub. Date: Dec. 6, 2018

(65) Prior Publication Data
US 2020/0121224 A1    Apr. 23, 2020

(30) Foreign Application Priority Data
May 30, 2017  (EP) .................................. 17173347

(51) Int. Cl.
*A61B 5/11* (2006.01)
*A61B 5/00* (2006.01)

(52) U.S. Cl.
CPC .......... *A61B 5/1102* (2013.01); *A61B 5/7225* (2013.01); *A61B 2562/0219* (2013.01)

(58) Field of Classification Search
CPC ............................ A61B 5/7225; A61B 5/1102
See application file for complete search history.

(56) References Cited

U.S. PATENT DOCUMENTS

| | | | |
|---|---|---|---|
| 9,167,975 B1 * | 10/2015 | Brady | ................... A61B 5/7296 |
| 2006/0293605 A1 | 12/2006 | Zanetti et al. | |
| 2012/0088982 A1 * | 4/2012 | Rulkov | ................... A61B 5/725 |
| | | | 600/301 |
| 2012/0296221 A1 | 11/2012 | Morren | |

(Continued)

FOREIGN PATENT DOCUMENTS

WO    2016134936 A1    9/2016

OTHER PUBLICATIONS

International Search Report and Written Opinion, International Application No. PCT/EP2018/063095, dated Jul. 2, 2018.

(Continued)

*Primary Examiner* — Rex R Holmes
*Assistant Examiner* — Jennifer L Ghand

(57) ABSTRACT

The invention provides a seismocardiograph system, which includes an accelerometer, adapted to obtain accelerometer data from user, and a bandpass filter, adapted to filter the accelerometer data. The system further includes an envelope filter, adapted to suppress S2 peaks in the band pass filtered accelerometer data, wherein the envelope filter comprises: a low-pass filter; and a comb filter, wherein the delay of the comb filter is tuned to a left ventricle ejection time (LVET).

16 Claims, 19 Drawing Sheets

(56) References Cited

U.S. PATENT DOCUMENTS

2016/0228069 A1    8/2016   Derkx et al.
2018/0028121 A1*   2/2018   Derkx ............... A61B 5/02438

OTHER PUBLICATIONS

Se Dong Min et al., "A Localization Method for First and Second Heart Sounds Based on Energy Detection and Interval Regulation", Journal of Electrical Engineering and Technology, vol. 10, No. 5, Sep. 2015.

Chaudhuri Anandeep et al., "Effective S1 S2 Detection System with Beat Track Method", 2016 IEEE.

R.M.M. Derkx and H. Duric, "Internal Specification of AtlasLib," Technical Note PR-TN 2011/00191, Philips Research Laboratories, Eindhoven (The Netherlands), Jul. 2011.

K. Tavakolian, Characterization and Analysis of Seismocardiogram for Estimation of Hemodynamic parameters, Ph.D. thesis, Simon Fraser University, Aug. 2010.

R.S. Crow, P. Hannan, D. Jacobs, and D.M. Salerno, "Relationship between seismocardiogram and echocardiogram for events in the cardiac cycle," Am. J. Noninvasive Cardiol., No. 8, pp. 39-46, 1994.

E.E. Eddleman, JR. Kathryn Willis, T.J. Reeves, and T.R. Harrison, "The Kinetocardiogram: I. Method of Recordings Precordial Movements," Circulation, vol. 8, pp. 269-275, 1953.

G. Amit, K. Shukha, N. Gavriely, and N. Intrator, "Respiratory modulation of heart sound morphology," Am. J. Physiol. Heart Circ., vol. 296, pp. 796-805, 2009.

Yang, C. et al., "Motion Noise Cancellation in Seismocardiogram of Ambulant Subjects with Dual Sensors", IEEE, 2016.

\* cited by examiner

SYSTEMS AND METHODS FOR SUPPRESSING PEAKS IN A SEISMOCARDIOGRAM

This application is the U.S. National Phase application under 35 U.S.C. § 371 of International Application No. PCT/EP2018/063095, filed on 18 May 2018, which claims the benefit of European Application Serial No. 17173347.0, filed 30 May 2017. These applications are hereby incorporated by reference herein.

FIELD OF THE INVENTION

This invention relates to the field of signal processing, and more specifically to the field of peak suppression in seismocardiograms.

BACKGROUND OF THE INVENTION

Respiratory and heart signals, and their corresponding rates, are fundamental vital signs for monitoring the condition of a patient. In particular, the heart rate is one of the most important vital signs for patient monitors on the ward. Typically the vital signals are generated through sensor electrodes attached to the patient; however, as patients are usually required to spend a significant amount of time on the ward, the attachment of electrodes and cables may become obtrusive and uncomfortable over an extended period of use.

In response to this, unobtrusive measurement techniques of respiratory and heart signals for patient monitoring are becoming increasingly popular. For example, a battery-powered tri-axial accelerometer may be attached to the body of a patient. In this case, the accelerometer may generate a seismocardiogram in order to determine the heart-rate.

Measuring vibrations caused by the mechanical activity of the heart started in the early 1900s by using the ballistocardiography (BCG) technique, where the blood transport causes small changes in center-of-gravity of a person, which can be measured by measuring the small displacements of a spring-mounted bed. As shown in FIG. 1, using a modern accelerometer 100, it is possible to measure the vibrations of the heart or blood-transport directly on the skin of a patient; a technique known as seismocardiography which measures the seismocardiogram (SCG) of the patient.

A typical analysis method used to obtain the average curves of the seismocardiogram signals is to use the R-peaks of an ECG measurement to segment the accelerometer data as shown in FIG. 2. For convenience, a typical SCG wave can be characterized by two main oscillations, namely, the S1 and S2 peaks representing the aortic valve opening and closing, respectively. In other words, the S1 peaks relate to the systolic contraction, whereas the S2 peaks relate to the end of the systole.

In order to obtain a heart rate from the seismocardiogram signals, the S1 peaks need to be detected and identified. Typically, a seismocardiograph system will include a classifier to assess the quality of the signals. For example, if the signal were to contain a large amount of movement artifacts, the classifier may classify the signal as bad.

In some cases, in particular in pediatric patients, the S2 peak may also be detected in addition to the S1 peak. This results in either: when the S2 peak is intermittently detected, the classifier identifying the S2 peak as an artifact, in which case, the signal is classified as bad and no heart rate is obtained; or, when the S2 peak is always detected, the system detects a heart rate measurement of double the true frequency.

There is therefore a need for a more reliable way to determine the heart rate within a seismocardiogram, and without requiring significant additional hardware.

Document WO 2016/134936 discloses a processing device for processing accelerometer signals for use in monitoring vital signs of a subject.

Document SE DONG MIN ET AL. discloses a method for the first and the second feature of heart sounds, based on an algorithm involving frequency filtering, energy detection, and interval regulation.

Document CHAUDHURI ANANDEEP ET AL discloses a method for detection of S1 and S2 heart sounds in both noised and de-noised environments.

SUMMARY OF THE INVENTION

The invention is defined by the claims.

According to examples in accordance with an aspect of the invention, there is provided a seismocardiograph system to obtain a seismocardiogram signal comprising:

an accelerometer, adapted to obtain accelerometer data from user;

a bandpass filter, adapted to filter the accelerometer data; and an envelope filter, adapted to suppress S2 peaks in the band pass filtered accelerometer data, wherein the envelope filter comprises:

a low-pass filter; and a comb filter, wherein the delay of the comb filter is tuned based on a left ventricle ejection time (LVET), wherein the delay of the comb filter is adaptively tuned by way of a first tuning parameter, $M_{cur}$, the adaptive tuning comprising:

applying a first prototype comb filter, having the first tuning parameter, $M_{cur}$, to the accelerometer data, wherein an output of the first prototype comb filter comprises an output of the envelope filter;

applying a second prototype comb filter, having a second tuning parameter, $M_{prev}$, to the accelerometer data;

applying a third prototype comb filter, having a third tuning parameter, $M_{forw}$, to the accelerometer data;

comparing a power output of the second prototype comb filter to a power output of the third prototype comb filter; and altering the first tuning parameter based on the comparison.

This system suppresses the S2 peaks in the seismocardiogram by way of the low-pass filter in combination with the comb filter. The comb filter operates under the assumption that the LVET, which corresponds to the time difference between the S1 and S2 peaks in a single heart cycle, is substantially constant. By using a comb filter having an input signal that is delayed by the LVET time and subsequently subtracted from the input signal, the signal is negatively adjusted at the moment of the S2 peaks, thereby suppressing the S2 peaks. Using the comb filter with a delayed input signal which is subsequently subtracted from the input signal, a series of notches spaced at regular frequency intervals in the frequency domain are obtained.

In addition, the bandpass filter may remove noise and movement artifacts from the accelerometer data, thereby further increasing the accuracy of the seismocardiogram.

By adaptively tuning the LVET delay in the comb filter, the system may adapt to more accurately suppress the S2 peaks of individual patients, thereby increasing the accuracy of the seismocardiogram.

In a further embodiment, the low-pass filter comprises an integrator filter.

In some designs, the accelerometer data comprises:
an x-axis component;
a y-axis component; and
a z-axis component, wherein the x, y and z-axis components are orthogonal to each other.

For an accelerometer attached to the skin of a patient, typically the accelerometer data will be strongest in the direction normal to the surface of the skin. This may vary depending on the orientation of both the accelerometer and the patient, meaning that by taking into account all three axes of accelerometer data, it is possible to record the vibrations in three orthogonal directions, thereby increasing the accuracy of the final seismocardiogram.

In some embodiments, the bandpass filter has a frequency range of 5 to 50 Hz, for example 10 to 40 Hz.

In this way, it is possible to eliminate accelerometer data relating to the breathing of the patient or the acceleration due to gravity, which is typically less than 5 Hz, and other noise and motion related artifacts, whist preserving the data relating to the heart rate of the patient.

In an embodiment, the integrator filter comprises a leaky integrator.

In this way, signals approaching DC frequencies, which typically contain any residual noise or artifacts, will be attenuated.

In an arrangement, the comb filter comprises a forward comb filter.

A forward or backward comb filter refers to the direction in which the signal is delayed before being summed with the non-delayed version of itself. In a forward comb filter, the input signal is delayed and subsequently added or subtracted to the input signal, whereas in a backward comb filter, the output signal is delayed and subsequently added or subtracted to the input signal.

In some arrangements, the system further comprises a rectifying unit adapted to calculate the absolute value of the bandpass filtered accelerometer data.

In an embodiment, the system further comprises a peak detector adapted to detect peaks in the envelope filtered accelerometer data.

In this way, it is possible for the system to identify the S1 peak frequency, which may then be used in the calculation of vital signs, such as heart rate, for the patient.

In a further embodiment, the system further comprises a classifier adapted to classify the peak detected accelerometer data.

In this way, the system may assess the quality of the accelerometer data to determine whether the system contains a large amount of noise or a large number of artifacts. If the signal does contain noise or artifacts, the classifier may classify accelerometer data as bad, indicating that it may not produce reliable information, such as vital signs.

According to examples in accordance with an aspect of the invention, there is provided a method for suppressing S2 peaks in a seismocardiogram, the method comprising:
obtaining accelerometer data;
applying a bandpass filter to the accelerometer data;
applying an envelope filter to the accelerometer data, thereby suppressing the S2 peaks in the accelerometer data, wherein the applying of the envelope filter comprises:
applying a low-pass filter; and
applying a comb filter, wherein the delay of the comb filter is tuned based on a left ventricle ejection time (LVET), wherein the delay of the comb filter is adaptively tuned by way of a first tuning parameter, $M_{cur}$, the adaptive tuning comprising:
applying a first prototype comb filter, having the first tuning parameter, $M_{cur}$, to the accelerometer data, wherein an output of the first prototype comb filter comprises an output of the envelope filter;
applying a second prototype comb filter, having a second tuning parameter, $M_{prev}$, to the accelerometer data;
applying a third prototype comb filter, having a third tuning parameter, $M_{forw}$, to the accelerometer data;
comparing a power output of the second prototype comb filter to a power output of the third prototype comb filter; and
altering the first tuning parameter based on the comparison.

In this way, it is possible to adapt the delay of the comb filter to more accurately match the LVET of an individual user. In addition, this may also allow for compensation for slight variations in the LVET between heart cycles.

In a further embodiment, the second tuning parameter is less than the first tuning parameter, which is less than the third tuning parameter.

By placing the second and third prototype filters either side of the first prototype filter, it is possible to more accurately adapt the first tuning parameter. For example, if the power output of the second prototype filter is larger than the power output of the third prototype filter, then the first tuning parameter may be reduced. Conversely, if the power output of the third prototype filter is larger than the power output of the second prototype filter, the first tuning parameter may be increased.

In an arrangement, the adaptive tuning of the delay of the comb filter further comprises:
applying a leakage factor to the first, second and third prototype comb filters, wherein the leakage factor is dependent on the first, second and third tuning parameters, respectively.

In this way, it is possible to normalize the behavior of comb filters with different tuning parameters at lower frequencies. In this way, the power of each of the outputs of the three prototype comb filters can be measured and the prototype comb filter most effective in the suppression of the S2 peaks may be identified.

In an embodiment, the adaptive tuning of the delay of the comb filter further comprises:
applying a scale factor to the first, second and third prototype comb filters, wherein the scale factor is dependent on the first, second and third tuning parameters, respectively.

By applying a scale factor to the prototype comb filters, the output powers may be normalized. In this way, it is possible to perform a more accurate comparison between the output powers of the three prototype comb filters, thereby leading to a more accurate adaption of the first tuning parameter.

In an embodiment, the method further comprises calculating an absolute value of the bandpass filtered accelerometer data.

In an arrangement, the method further comprises detecting peaks in the envelope filtered accelerometer data.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a seismocardiograph system, which includes an accelerometer, adapted to obtain accelerometer data from user, and a bandpass filter, adapted to filter the accelerometer data. The system further includes an envelope filter, adapted to suppress S2 peaks in the band pass filtered accelerometer data, wherein the envelope filter comprises: a low-pass filter; and a comb filter, wherein the delay of the comb filter is tuned to a left ventricle ejection time (LVET).

Figure 3:
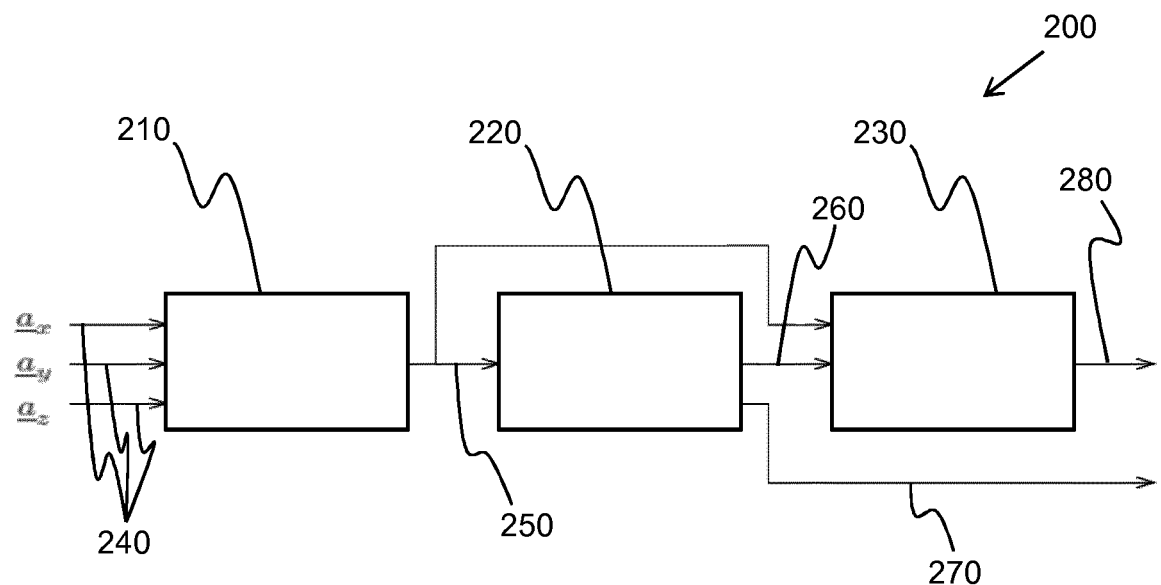
FIG. 3 shows a schematic of a seismocardiograph system.

FIG. 3 shows a schematic diagram of a seismocardiograph system 200.

Figure 1:
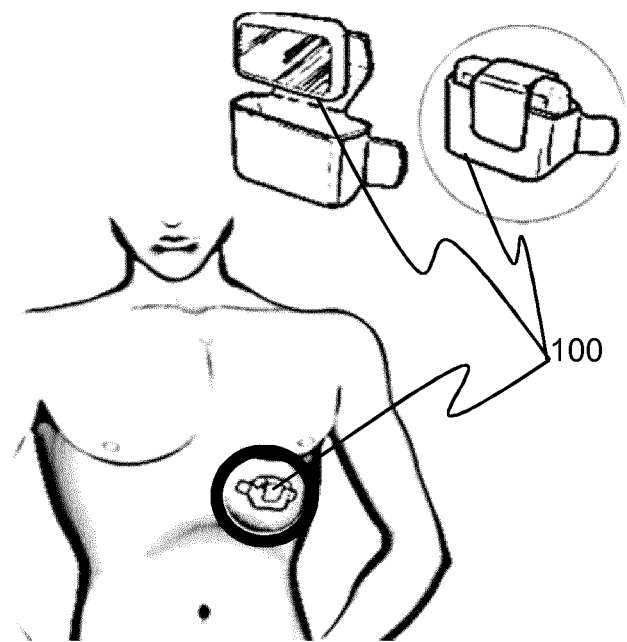
FIG. 1 shows an accelerometer, adapted to obtain accelerometer data for a seismocardiogram, attached to the skin of a patient.

The system comprises: a pre-processor 210, which is described in more detail with reference to FIG. 4; a peak detector 220; and a classifier 230. The pre-processor obtains accelerometer data 240 from an accelerometer, such as the accelerometer 100 shown in FIG. 1. In this case, the accelerometer data comprises acceleration components: $a_x$; $a_y$; and $a_z$, in three orthogonal axes: x-axis; y-axis; and z-axis, respectively. The pre-processor filters the accelerometer data, combines the axial data into a single set of accelerometer data and determines an envelope of the fused signal.

Figure 2:
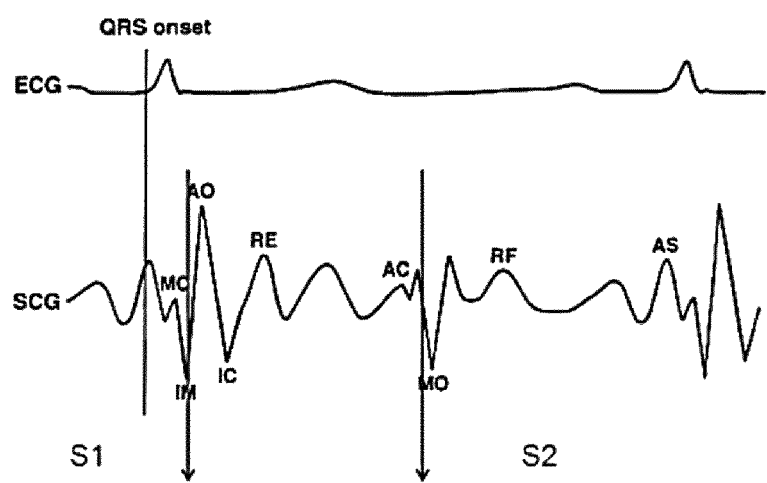
FIG. 2 shows a typical SCG signal, segmented using an ECG signal.

Following the pre-processing step, the envelope signal 250 is provided to both the peak detector 220 and the classifier 230. The peak detector is adapted to detect peaks, either maxima or minima, in the envelope signal. Referring to FIG. 2, the peak detector may be adapted to detect the AO peak within the S1 oscillation, which is associated with the opening of the aortic valve. The peak detections 260 are then provided to the classifier in order to check the quality of the signal. In addition, the detected peaks may be supplied as a separate signal 270 to form the basis of a vital sign of a patient, such as the heart rate.

The classifier 230 is provided with the envelope signal 250 and the peak detections 260. The classifier may compute features of the envelope signal and the peak detections over a time window, for example 8 seconds. The classifier may then assess these features based on a known wave-shape model, which may be used due to the similarities in the morphology of a heart-cycle. If the classifier determines that the envelope signal contains a large amount of noise or movement artifacts, it may produce a label 280 indicating that the envelope signal, and so the associated vital sign, is inaccurate. Alternatively, if the signal does not contain a significant amount of noise or artifacts, the classifier may produce a label indicating that the envelope signal is accurate.

Figure 4:
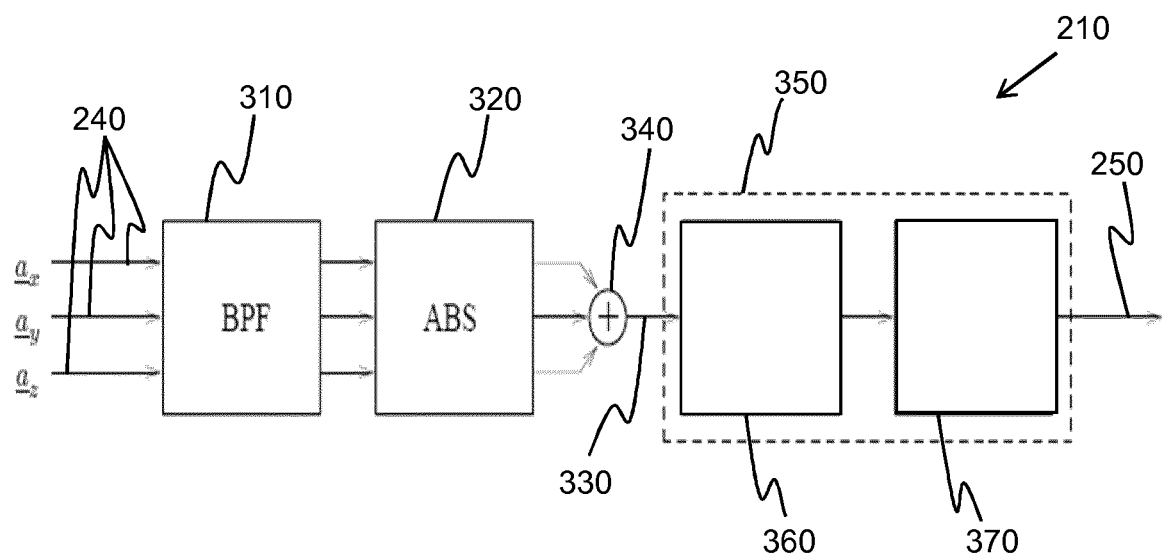
FIG. 4 shows a schematic of the pre-processing part of the system of FIG. 3.

FIG. 4 shows a schematic representation of the pre-processor 210 of the system 200 of FIG. 3.

The obtained accelerometer data 240 are first provided to a bandpass filter 310. The bandpass filter is adapted to remove signals relating to the breathing of the user and the acceleration due to gravity, in addition to other noise and motion related artifacts. The band pass filter may have a range of 10-40 Hz in order to remove the breathing frequencies, which are typically below 5 Hz. Alternatively, the bandpass filter may be replaced by a high pass filter, operating for example at 10 Hz, in series with a low pass filter, operating for example at 40 Hz.

The bandpass filtered signals may then be provided to a rectifying unit 320, adapted to compute the absolute value of each of the accelerometer data signals. The absolute accelerometer data signals may then be combined into a single accelerometer signal 330 by way of a summation unit 340. The single accelerometer signal is then provided to an envelope filter 350, which comprises a low-pass filter 360 and a comb filter 370.

The envelope filter, comprising the low-pass, is designed to be a low-pass filter combined with a comb filter. For example, the envelope filter may comprise one or more integrator filters in series followed by one or more comb filters. Alternatively, the envelope filter may comprise two integrator filters separated by one or more comb filters. As the components of the envelope filter employ linear signal processing techniques, the integrator filters and comb filters may be arranged in any order.

For the integrator filters, a leaky integrator may be used, as shown by plot 400 in FIG. 5, which is described by the equation below:

$$F(z) = \frac{1}{1 - \gamma z^{-1}},$$

where: γ is a constant less than 1 and z is the delay operator for the Z-transform.

A comb filter may operate by adding a delayed and scaled version of a signal to itself, thereby generating either constructive or destructive interference depending on the scale factor. In this case, a forward comb filter may be used, which is described by the following transfer function:

$$H(z)=b_0+b_M z^{-M},$$

where: H(z) is the transfer function of the comb filter; $b_0$ and $b_M$ are selectable scale factors for the equation; and M is a constant.

Alternatively, the comb filter may also operate by subtracting a delayed and scaled version of a signal from itself, thereby negatively adjusting the signal at the subtraction point. In the examples described herein, $b_0=-b_M$, where $b_0$ has a positive value and hence $b_M$ has a negative value.

Figure 5:
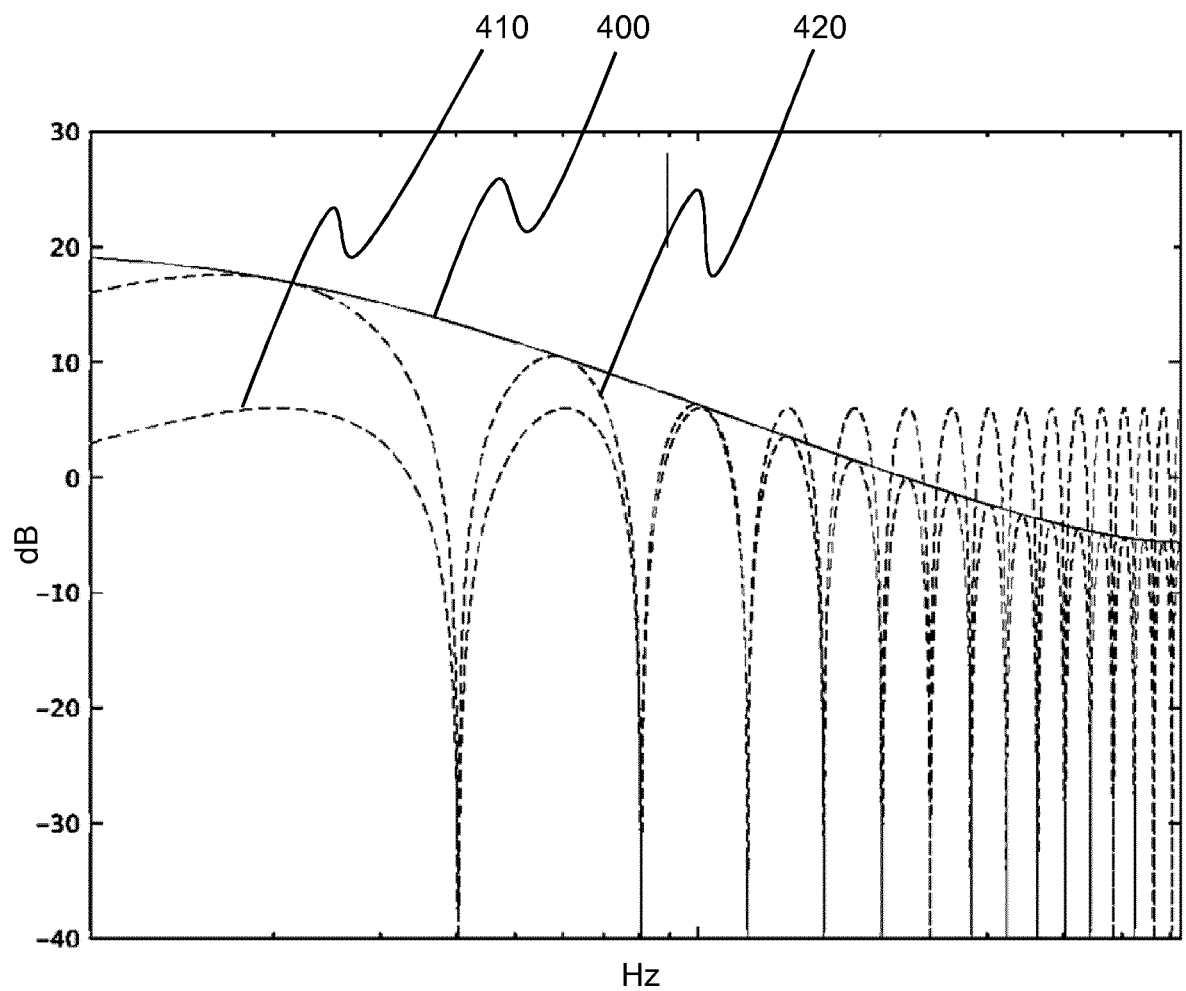
FIG. 5 shows a plot of the leaky single integrator filter and the comb filter, in the frequency domain, when taken individually and when combined.

The frequency response of the comb filter, as shown by plot 410 in FIG. 5, comprises a series of notches. It should be noted that the x-axis of FIG. 5 is logarithmic and so the notches of the comb filter occur at regular intervals.

The constant M defines the location of the first notch frequency, and so the spacing between the notches of the comb filter. The larger the value of M, the lower the first notch frequency and the more often a notch occurs. The value of M may be chosen in order to negatively adjust the output signal of the comb filter at the moment an S2 oscillation of a heart cycle occurs. This can be achieved by calculating a value for M based on a feature of the heart cycle; namely, the Left Ventricle Ejection Time (LVET) of the user, the time between the AO (S1 oscillation) and AC (S2 oscillation) peaks as shown in FIG. 2, which remains substantially constant over time. In this case, the value for M may be calculated using the following floor function:

$$M=\lfloor t_{LVET} F_s \rfloor,$$

where: $t_{LVET}$ is the LVET of the user; and $F_s$ is the sampling frequency of the accelerometer signal.

The combination of the leaky integrator and the comb filter is shown by plot 420 in FIG. 5. The combination of the integrator and the comb filter provides a sufficient enhancement of the low frequencies in the seismocardiogram together with a suppression of the S2 oscillations in the seismocardiogram. In addition, the leaky factor of the leaky integrator provides attenuation for signals approaching DC frequencies. To further increase enhancement of the low frequencies in the seismocardiogram, we can apply this combination of an integrator with a comb filter twice.

Figure 6:
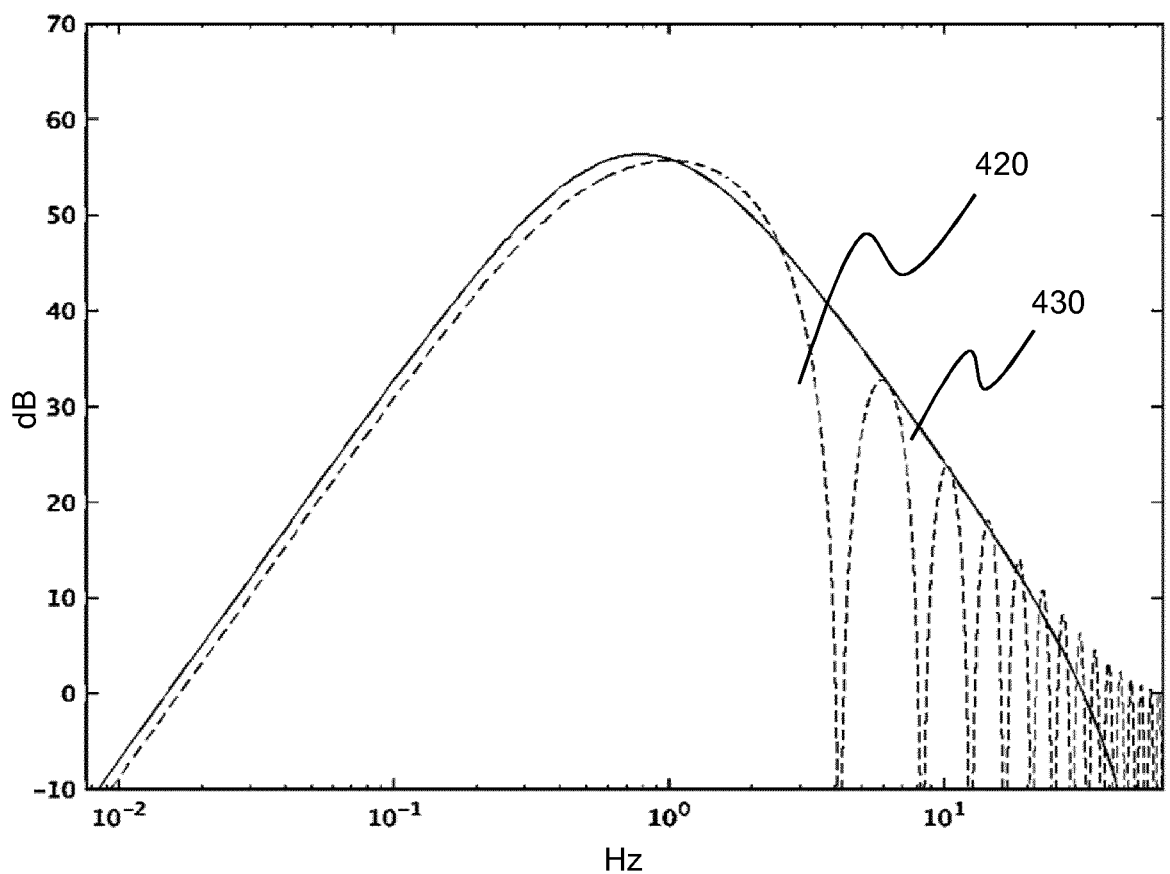
FIG. 6 shows a plot of the combined leaky double integrator and two comb filters in comparison to a leaky double integrator combined with two first order Butterworth high pass filters having a cutoff frequency of 0.6 Hz.

FIG. 6 shows a comparison between the frequency response of an envelope filter that includes a series of two integrators combined two comb filters 420, as described above, and an envelope filter that includes a series of two integrators combined with a high pass filter 430. As can be seen from the Figure, the second envelope filter 430 provides the attenuation for close to DC frequencies in a similar manner to the first envelope filter 420; however, the second envelope filter does not provide the modulation of the comb filter, meaning that the S2 peaks of the accelerometer data are not suppressed. The resulting envelope signals from these two envelope filters are shown in FIGS. 7 and 8.

Figure 7:
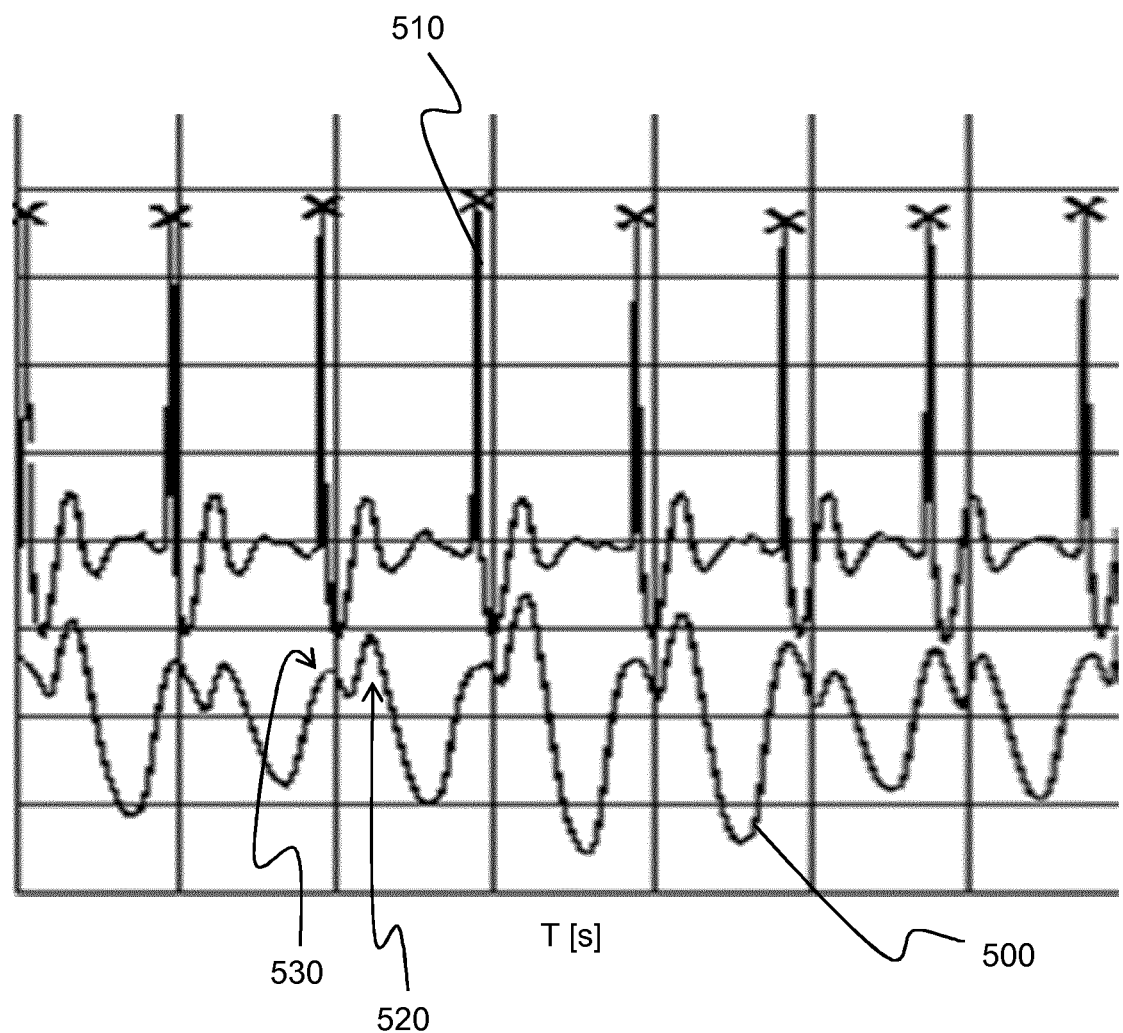
FIG. 7 shows a typical SCG envelope signal and reference signal for an envelope filter that does not include a comb filter.

FIG. 7 shows an SCG envelope signal 500 for the second envelope filter 430, shown in FIG. 6. In addition, a reference signal 510, such as an ECG signal is provided. It is clear to see from this plot that the S2 peaks 520 of the envelope signal often dominate over the S1 peaks 530. As a result, a peak detector would not detect the S1 peaks and erroneously detect the S2 peaks. As the trigger for the classifier of the signal to detect a bad signal is based on either peak-to-peak variability or waveform morphologies with the peaks as fiducial points, the classifier would classify the signal as being a bad signal. Alternatively, when the peak detector detects both the S1 and S2 peaks, the classifier may classify the signal as being a good signal, which will erroneously lead to a heart rate of double the frequency obtained from the reference signal.

Figure 8:
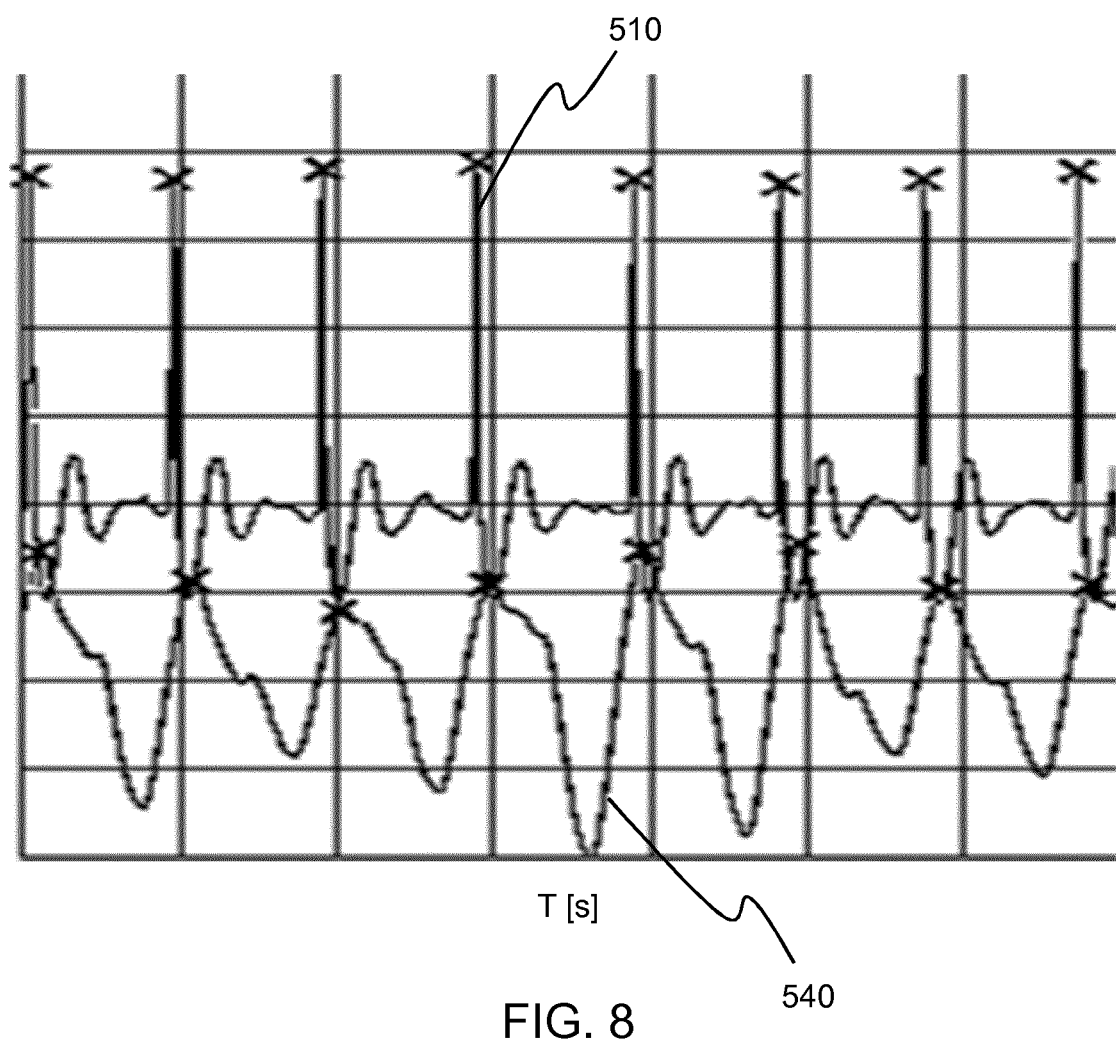
FIG. 8 shows the SCG signal and reference signal for an envelope filter that includes a comb filter.

FIG. 8 shows an SCG envelope signal 540 for the first envelope filter 420, shown in FIGS. 5 and 6. Once again, the reference signal 510, such as an ECG signal is provided. In this case, the S2 peaks have been suppressed, meaning that the SCG signal comprises a single peak for each heart cycle. This leads to an improved signal quality and a more consistent detection of the S1 peaks, leading to improved heart rate detection.

An example of a cycle of the S2 peak suppression method is described with reference to FIGS. 9 to 17.

Figure 9A:
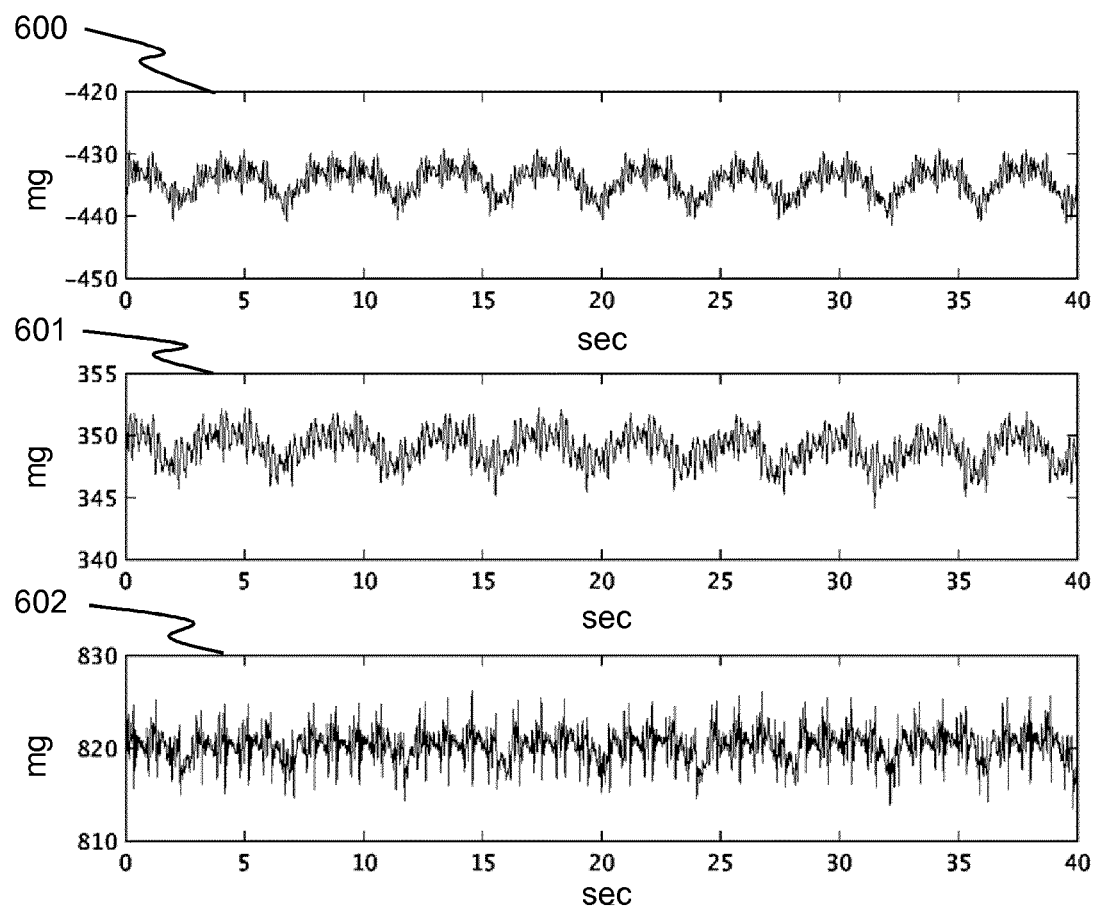
FIGS. 9A and 9B show an example of raw accelerometer data in the time and frequency domains, respectively.

FIG. 9A shows the accelerometer signals in the time domain across three orthogonal axes. The top graph 600 corresponds to the x accelerometer axis, the middle graph 601 corresponds to the y accelerometer axis and the bottom graph 602 corresponds to the z accelerometer axis. The y-axis of the three graphs is measured in units of milli-g, where g is the acceleration due to gravity. It can be seen that for each accelerometer axis, there is an offset that depends on gravity and the orientation of the sensor. Furthermore, it can be seen that there is a modulation of the offset that corresponds to the respiration. In FIG. 9A, we can see around 9 breath cycles.

Figure 9B:
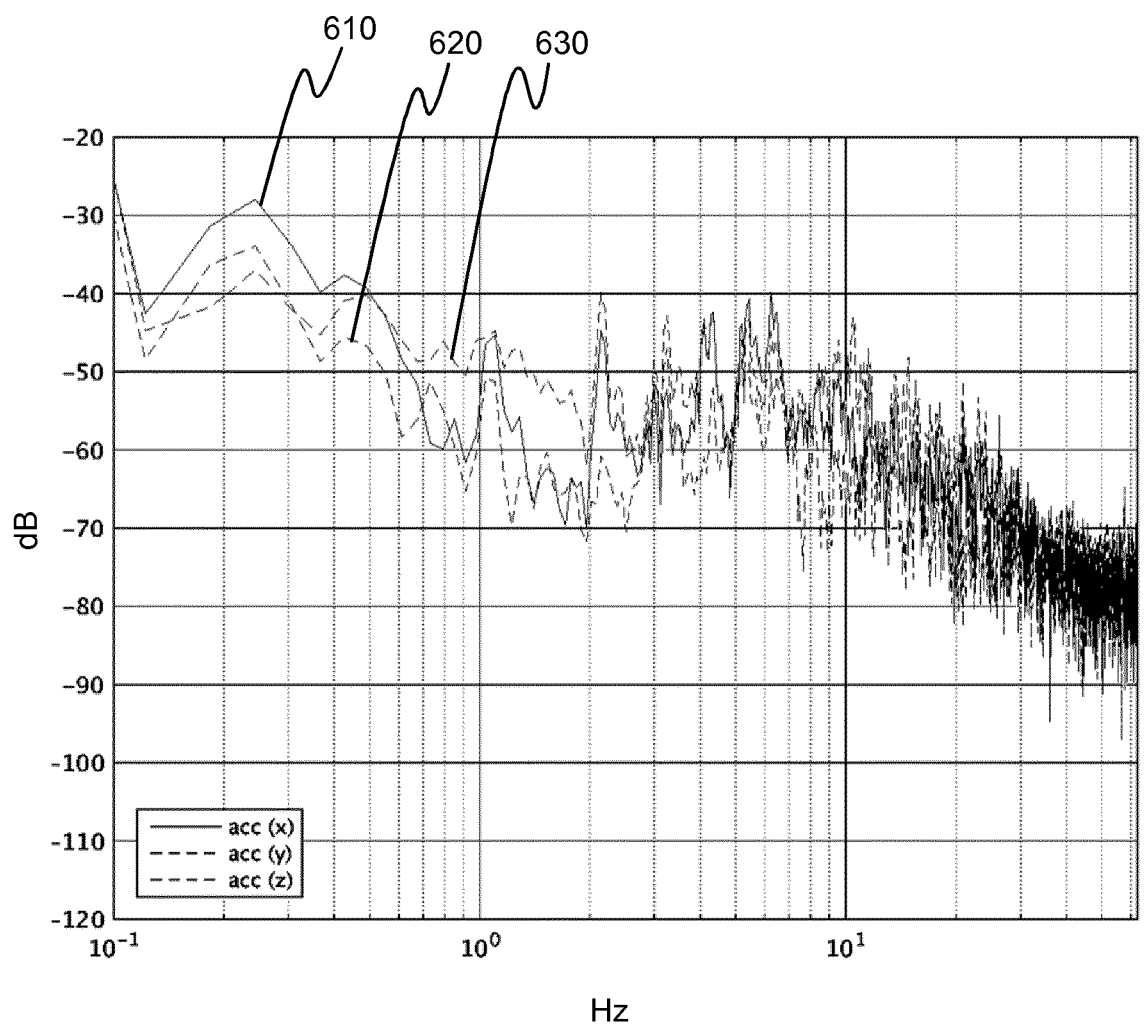

FIG. 9B shows a graph of accelerometer data in the frequency domain, from a patient across three orthogonal axes, namely, the x accelerometer 610, y accelerometer 620 and z accelerometer 630 axial data. In this case, the z axis is defined as being normal to the surface of the skin of the patient. From the graph, it is clear that the low frequency signals are dominant; however, this is because there is a baseline signal in each of the three axes that is determined by the constant acceleration due to gravity and the orientation of the sensor. Depending on the orientation, the axes include a certain amount of the acceleration due to gravity. This gravity component is very strong compared to the accelerations due to the heartbeats.

Figure 10:
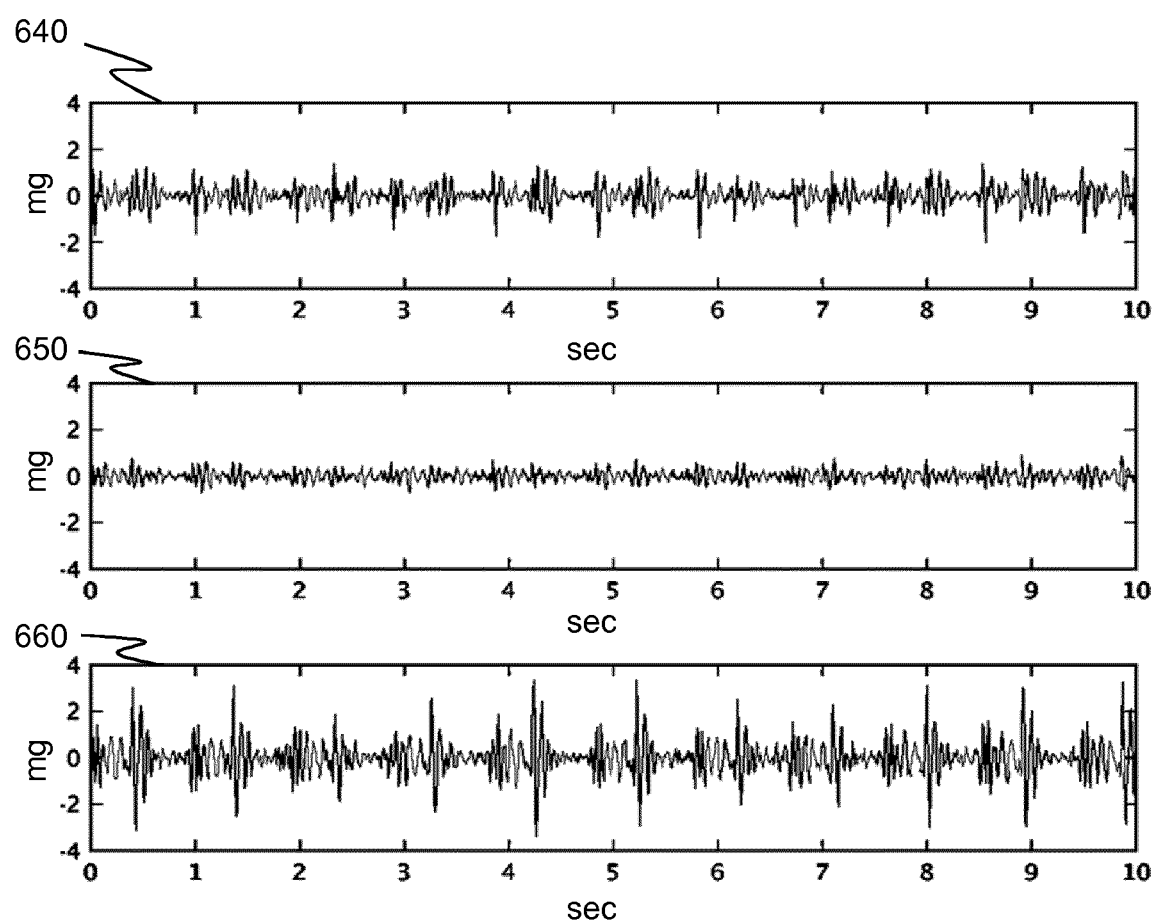
FIG. 10 shows the accelerometer data of FIG. 9 in the time domain after the application of a bandpass filter.

FIG. 10 shows the same signals as in FIG. 9A, in the time domain, but after passing through a bandpass filter. In this case, the band of the bandpass filter is set to 10 to 40 Hz, thereby removing the low frequency accelerations due to gravity. The y-axis is measured in units of milli-g, where g is the acceleration due to gravity. The top graph 640 corresponds to the x accelerometer axis data 600, the central graph 650 corresponds to the y accelerometer axis data 601 and the bottom graph 660 corresponds to the z accelerometer axis data 602.

As can be seen in FIG. 10, the bottom graph 660 corresponding to the z axis of the accelerometer shows the strongest acceleration signal. In some cases, only the z axis may be used as the accelerometer data in the method described above. Alternatively, as the remaining axes such as the x axis as shown in the top graph 640 may also contain strong accelerometer signals, the three accelerometer signals may be fused into a single accelerometer data signal before entering the envelope filter.

Figure 11:
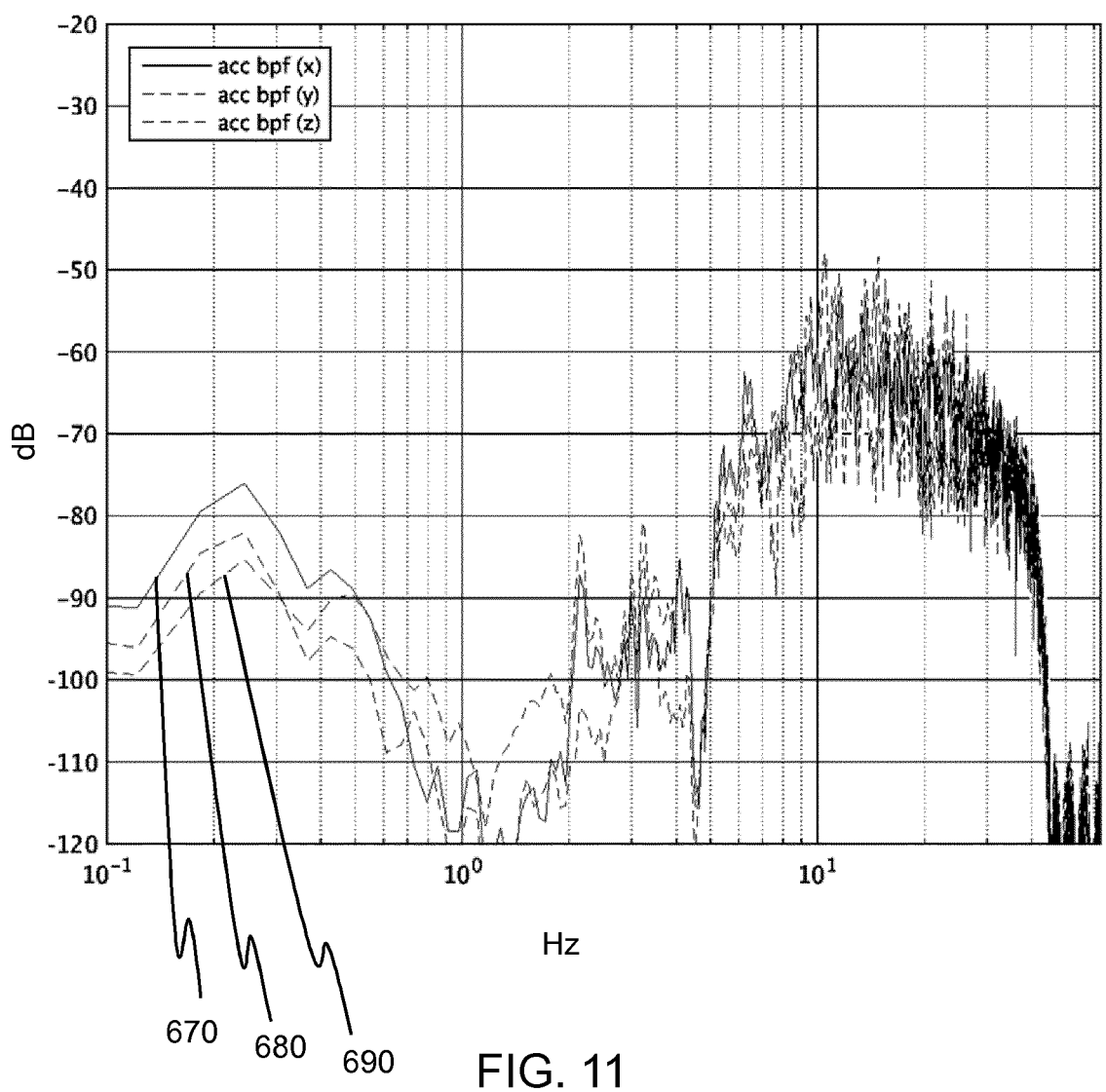
FIG. 11 shows the accelerometer data of FIG. 9 in the frequency domain after the application of a bandpass filter.

FIG. 11 shows the signals of FIG. 10 in the frequency domain, wherein: plot 670 corresponds to the x axis signal of the top graph 640; plot 680 corresponds to the y axis signal of the central graph 650; and plot 690 corresponds to the z axis plot of the bottom graph 660.

Figure 12:
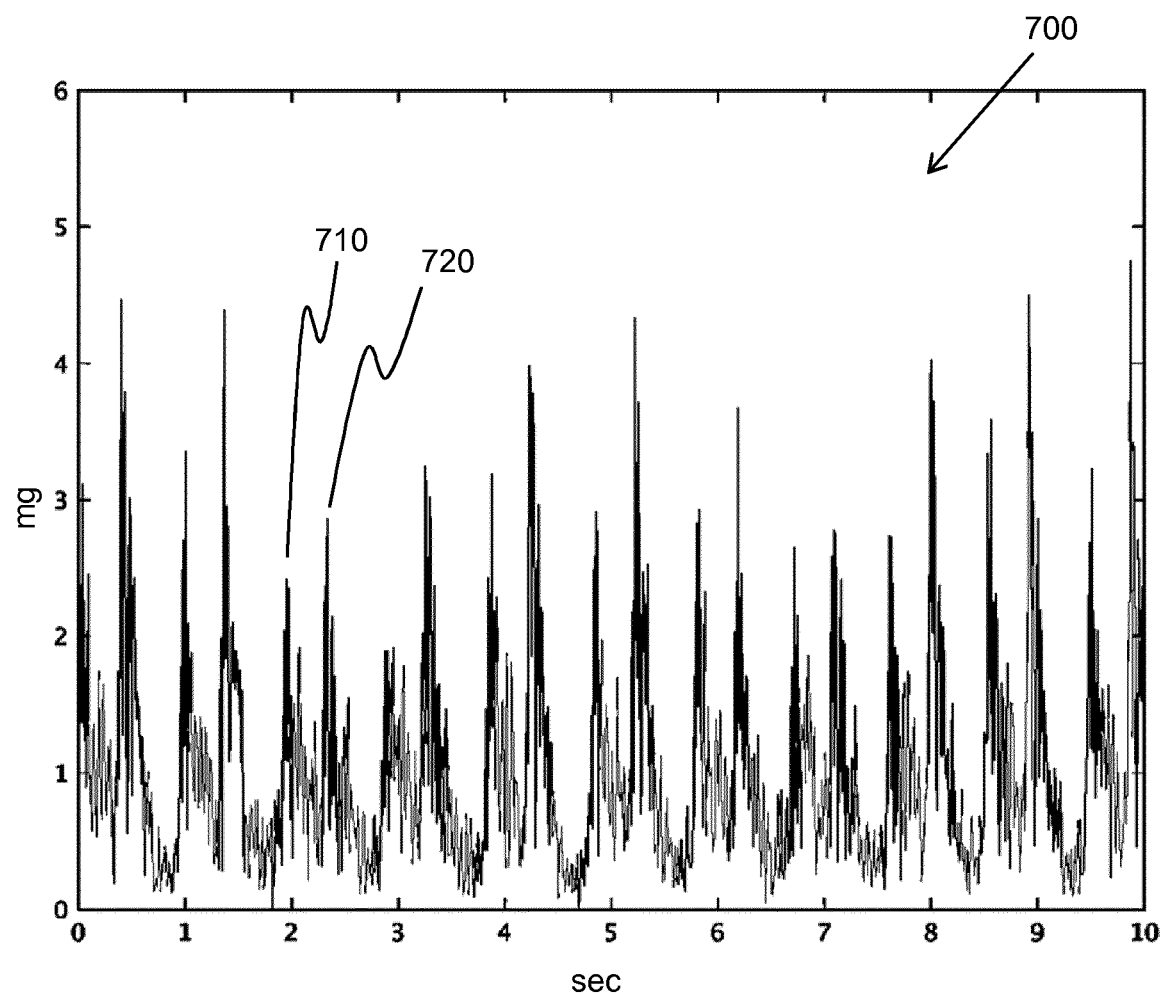
FIG. 12 shows the summation of the absolute values of accelerometer data of FIGS. 10 and 11 in the time domain.

Following the bandpass filtering of the accelerometer data, the absolute values of the accelerometer signals are summed, leading to the signal 700 shown in FIG. 12. As can be seen, the signal has only positive valued samples due to the nonlinear operator (absolute value).

The presence of both S1 710 and S2 720 peaks is very clear in FIG. 12. Hence, there is a need for an envelope filter which only passes the S1 peaks and suppresses the S2 peaks.

Figure 13:
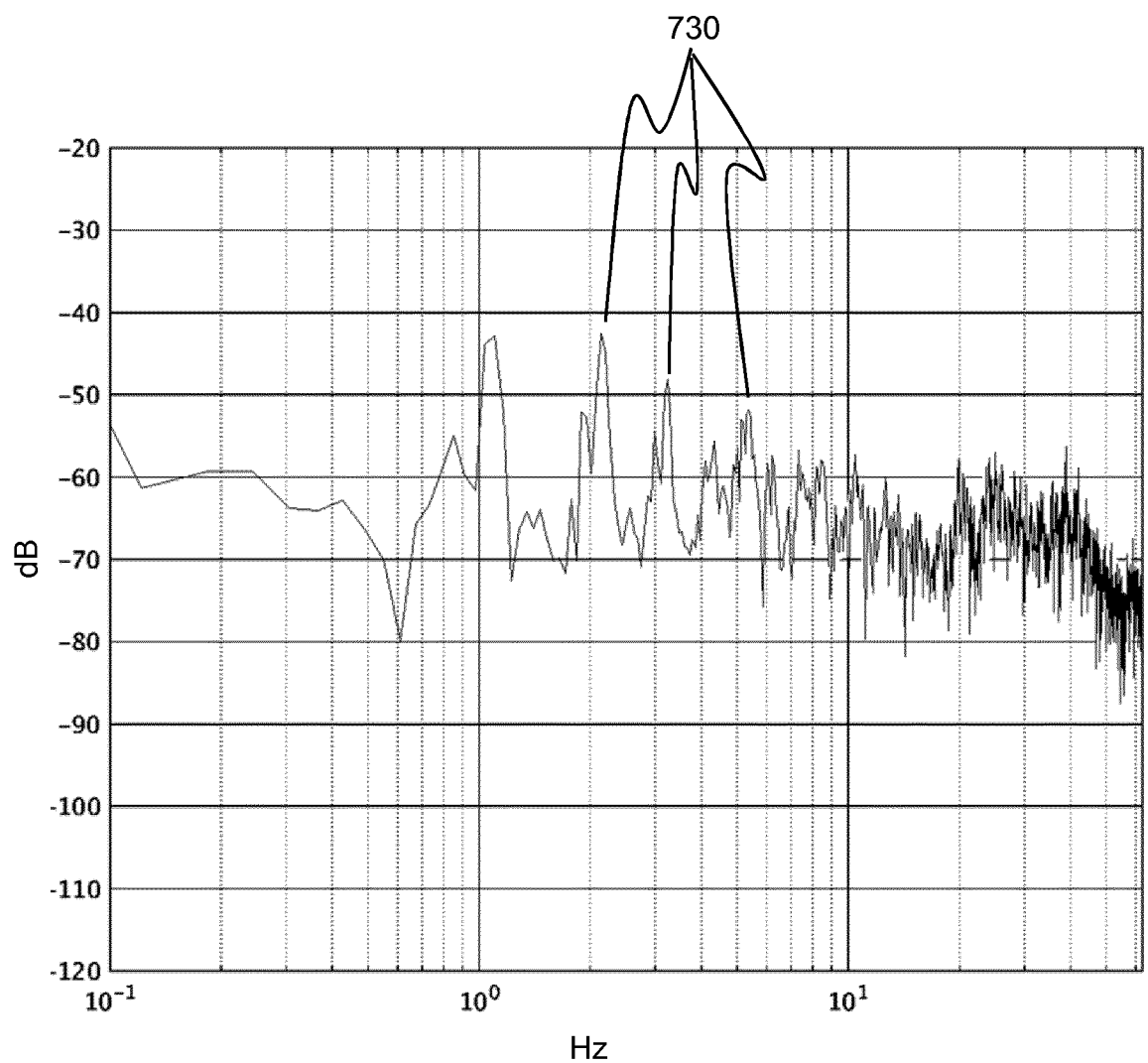
FIG. 13 shows the summation of the absolute values of accelerometer data of FIGS. 10 and 11 in the frequency domain.

FIG. 13 shows the frequency domain plot of the time domain signal of FIG. 12. As can be seen, the frequency changes due to the nonlinear operator (absolute value), meaning that the lower frequencies are again present. The harmonics 730 in the frequency spectrum of the summed accelerometer data, which may be seen in the frequency domain plot in FIG. 13, are related to both S1 and S2 peaks; however, there is a temporal relation between the S1 and S2 peak that is not visible in the magnitude frequency spectrum of FIG. 13.

Figure 14:
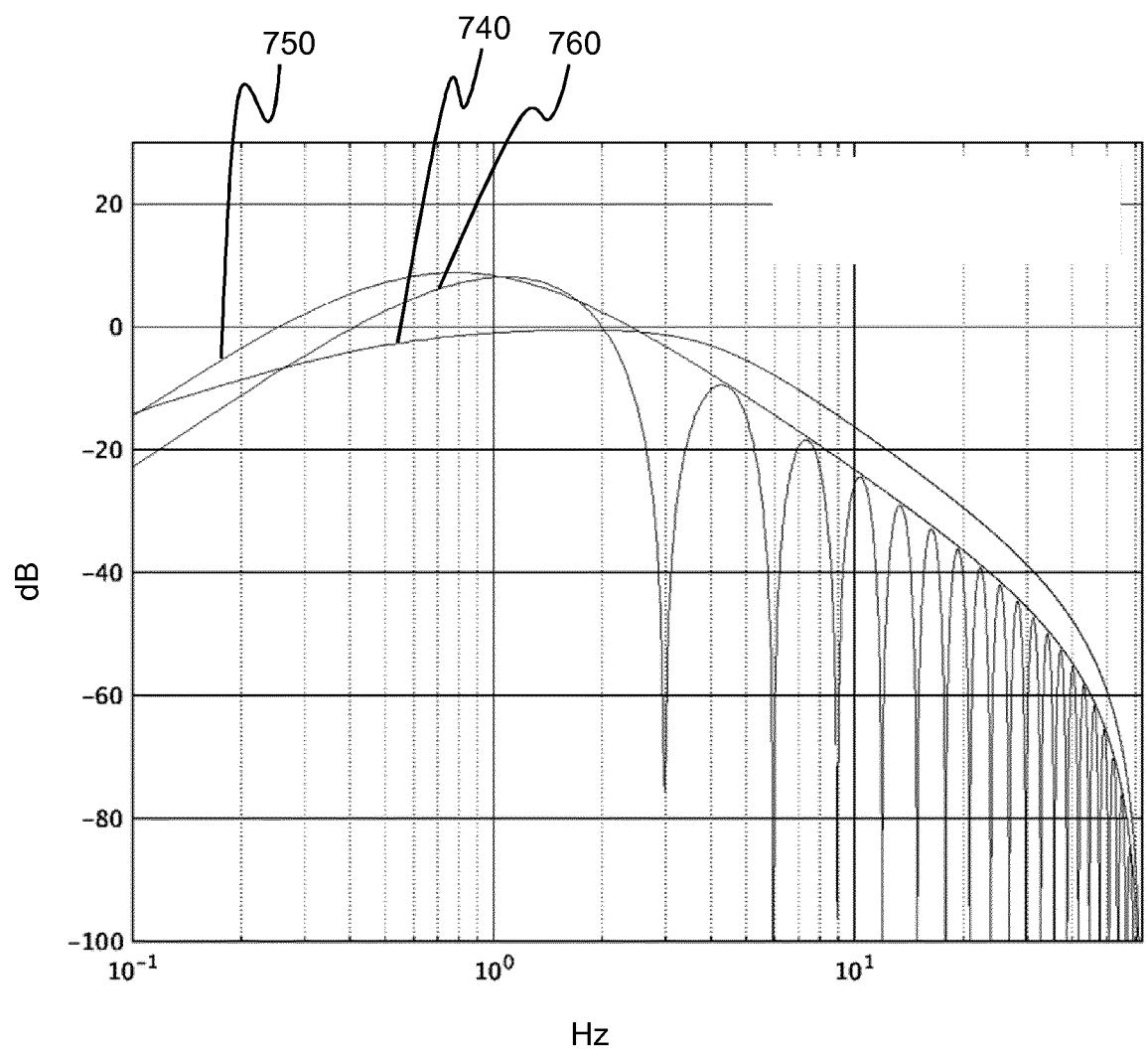
FIG. 14 shows three examples of envelope filters.

In this example, the behavior of three different envelope filters is shown. The frequency responses of the three envelope filters are shown in FIG. 14. The first filter 740, also referred to as 1BPF, is a bandpass filter designed via a series concatenation of a second order Butterworth low-pass filter with cutoff frequency of 4 Hz and a first order Butterworth high-pass filter with cutoff frequency of 0.5 Hz. The second filter 750, also referred to as 2intHPF, comprises a double leaky integrator filter and two first order Butterworth high-pass filters with cutoff frequency of 0.6 Hz connected in series. The third filter 760, also referred to as 2intCF, comprises a double leaky integrator and two comb filters, as described in FIG. 5.

Looking to the 2intCF envelope filter 760, in this example the LVET has been tuned to 0.33 sec, which gives the first notch of the comb filter set to around 3 Hz. Looking back to FIG. 13, this means that the third harmonic, sixth harmonic, etc. is suppressed, which contain a significant part of the energy belonging to S2.

Figure 15:
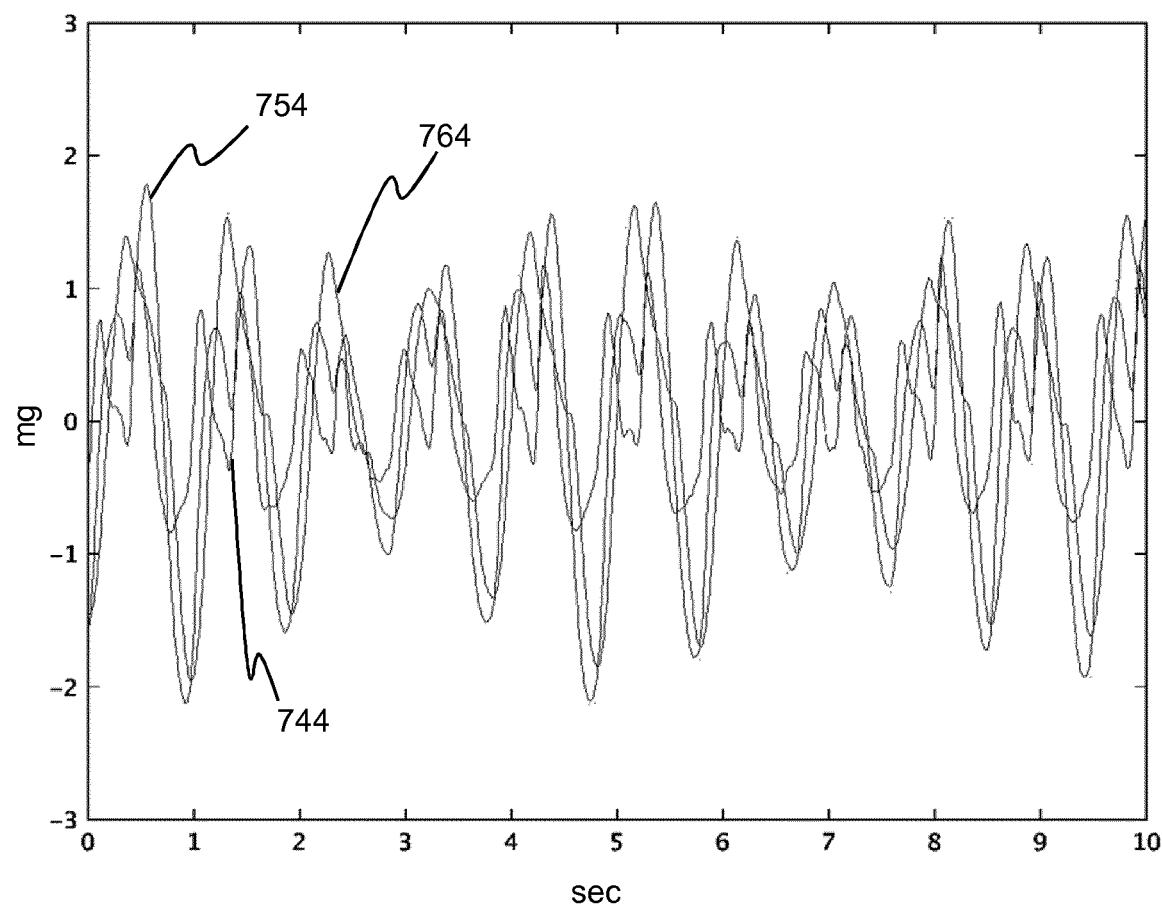
FIG. 15 shows the output of the three envelope filters of FIG. 14 in the time domain.
Figure 16:
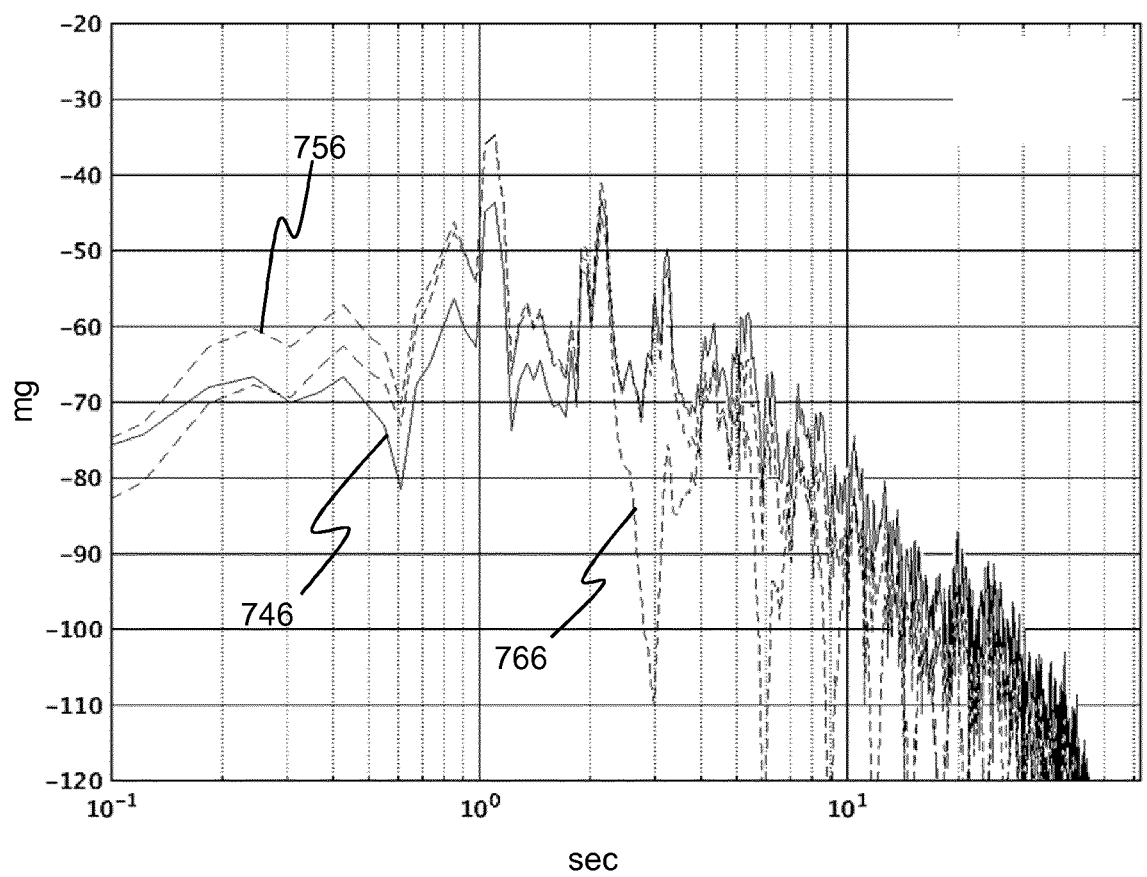
FIG. 16 shows the output of the three envelope filters of FIG. 14 in the frequency domain.

FIGS. 15 and 16 show the output of the three envelope filters of FIG. 14 in the time and frequency domains, respectively. Plots 744 and 746 depict the time and frequency domain responses of the 1BPF envelope filter 740. Plots 754 and 756 depict the time and frequency domain responses of the 2intHPF envelope filter 750. Plots 764 and 766 depict the time and frequency domain responses of the 2intCF envelope filter 760. It is clear to see, in plot 766, the notches introduced by the comb filter of 2intCF at every $3^{rd}$ harmonic of the accelerometer data, thereby suppressing a significant part of the energy belonging to the S2 peaks.

Figure 17:
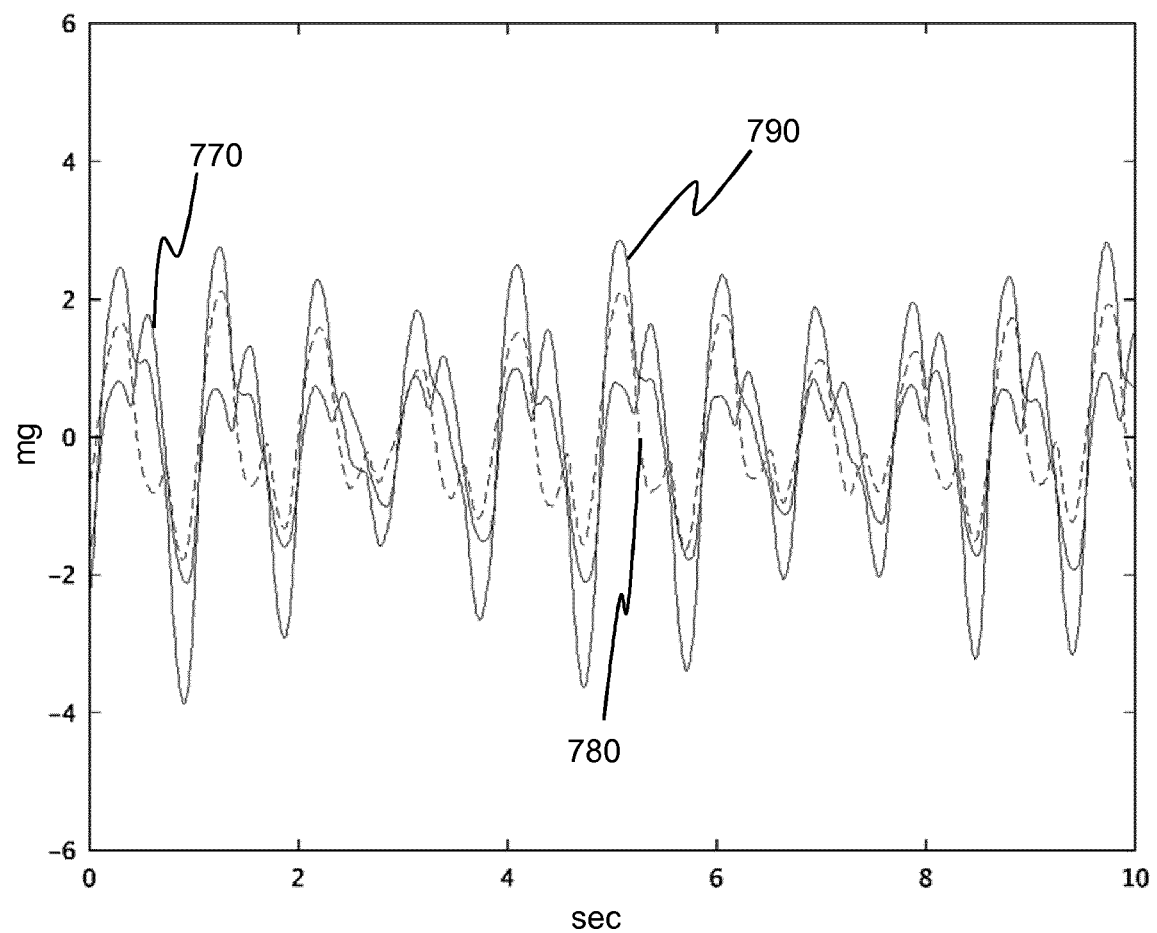
FIG. 17 shows the combination of two intermittent signals in a feedforward comb filter in the time domain to illustrate the construction of the output of the comb filter.

As described above, the comb filter operates by subtracting a delayed version of a signal to itself. Hence, the application of the comb filter on the 2intHPF signal 754 may be interpreted as subtracting a delayed version of the signal 754 from the signal 754 itself. FIG. 17 shows the visualization of this subtraction. The first signal 770 being the 2intHPF signal 754 of FIG. 15 and the second signal 780 being the negated 2intHPF signal of FIG. 15, which is delayed by M=41 samples. The summation of these two, original 770 and delayed+negated 780 signal, is shown by signal 790. As can be seen in signal 790, the S2 peaks have been reduced and the S1 peaks have been enhanced.

The envelope filter may be configured to adapt to users with different LVETs. More specifically, the value of the tuning parameter, M, in the comb filter may be adapted to a user during the operation of the seismocardiograph system. This may be done via an iterative update process.

The iterative update of the LVET may be performed as follows. Three prototype comb filter designs, having different values of M, are applied to the accelerometer data. The first tuning parameter, associated with the first prototype comb filter, is defined as $M_{cur}=\lfloor t_{LVET} F_s \rfloor$, as described above. The output of the first prototype comb filter is used as the output signal of the pre-processing as normal. In addition, there are two other prototype filters having a second tuning parameter, $M_{prev}=M_{cur}-1$, and a third tuning parameter, $M_{forw}=M_{cur}+1$. For example, when $t_{LVET}=0.24$ s and $F_s=125$ Hz: $M_{cur}=30$; $M_{prev}=29$; and $M_{forw}=31$.

Figure 18:
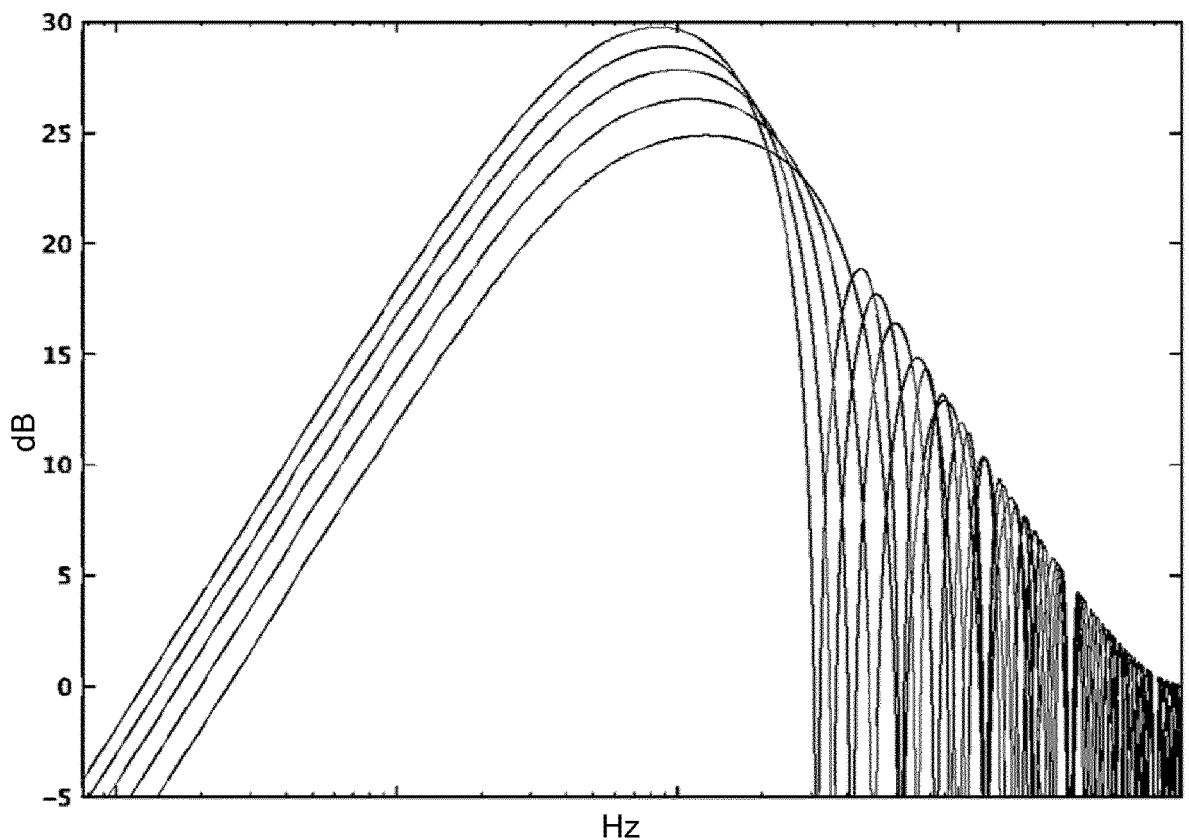
FIG. 18 shows the frequency response of the combined leaky double single integrator and comb filter for different tuning parameters.

FIG. 18 shows the frequency responses for a leaky integrator combined with a comb filter, referred to as a single leaky integrator with comb filter, for different values of M. From the Figure it is clear to see that the single leaky integrator with comb filter exhibits different behaviours at low frequencies for different values of M. This is known as roll-off. To compensate and equalize the roll-off in the lowest frequencies, a different leakage factor, γ, may be applied to each of the three prototype single leaky integrator with comb filters. The leakage factors are given by:

$$\gamma = 1 - 0.0008 M_i,$$

where $M_i \varepsilon \{M_{cur}, M_{prev}, M_{forw}\}$.

Figure 19:
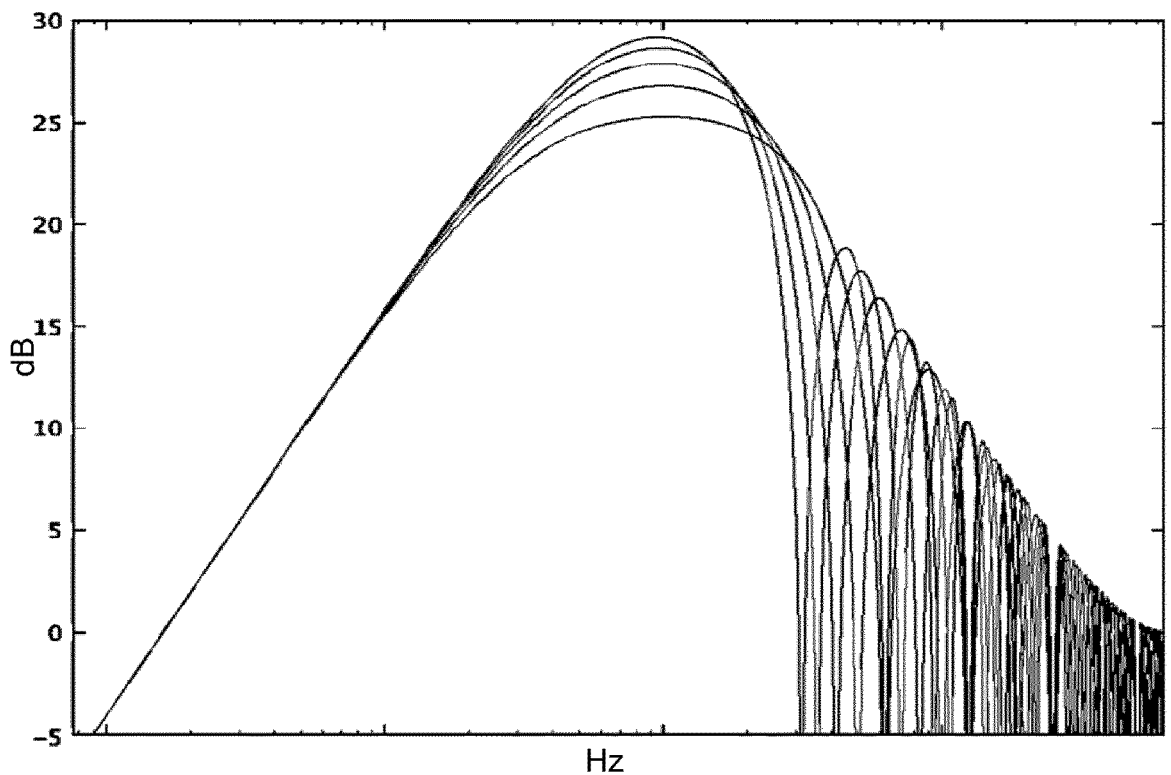
FIG. 19 shows the frequency response of the combined leaky single integrator and comb filter for different tuning parameters after the application of the leakage parameter.

The resulting (compensated roll-off) frequency responses for the single leaky integrator with comb filter across different values of M are shown in FIG. 19.

In order to ensure equal power responses from the prototype single leaky integrator with comb filters, a scale factor, s, is defined as:

$$s = \sqrt{1.5825 - 0.0165 M}.$$

Figure 20:
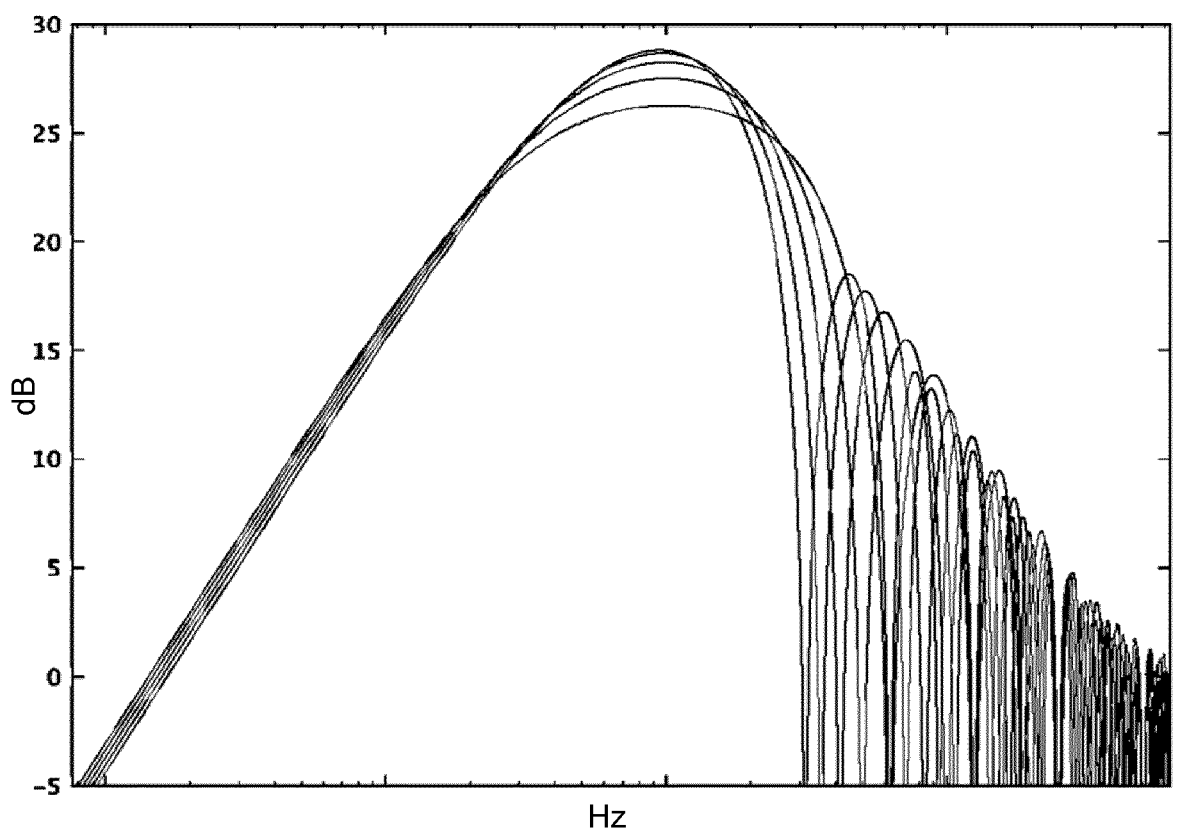
FIG. 20 shows the frequency response of the combined leaky single integrator and comb filter for different tuning parameters after the application of the scale factor.

The scale factor leads to a normalization of the prototype single leaky integrator with comb filter responses with respect to their total power as shown in FIG. 20. The two corrections that have been applied to the prototype filters have led to a normalization of the responses in terms of power and shape, with the only main difference being the notch frequencies. As can be seen from FIG. 20, the roll-off in the lower frequencies is somewhat changed by the scale factor; however, the low-frequency behavior of the prototype single leaky integrator with comb filters remains very comparable between the values of M.

Following the correction of the responses, the algorithm may decide, based on comparison of the powers of the three output signals that come out of the double leaky integrators in series with the comb filters with $M_{prev}$, $M_{forw}$ and $M_{forw}$, in which direction the $t_{LVET}$ timing needs to be adapted. For example, a simple first-order recursive network may be used to estimate the power of the output-signals. The effective averaging time for the power estimates may, for example, be chosen as 2 seconds.

If the power of the double leaky integrator in series with the comb filters with tuning parameter $M_{prev}$ is larger than the power of the double leaky integrator in series with the comb filters with tuning parameter $M_{forw}$, then the LVET time may be reduced. Further, if the power of the double leaky integrator in series with the comb filters with tuning parameter $M_{forw}$ is larger than the power of the double leaky integrator in series with the comb filters with tuning parameter $M_{prev}$, then the LVET time may be increased.

It should be noted that $t_{LVET}$ may be adapted on a very fine-grained non-integer real-valued scale and then rounded to obtain the integer value of the delay M, such that the adaptation of the comb filter occurs very gradually. In addition, it is possible to stall the adaptation of M when the differences in the output power in each of the three responses are below a certain threshold.

It is not required to compute the three responses independently. The common factors of the integrator filter and the majority of the input delay line of the comb filter for the three responses can be shared. This may reduce both computational complexity and memory consumption.

Figure 21:
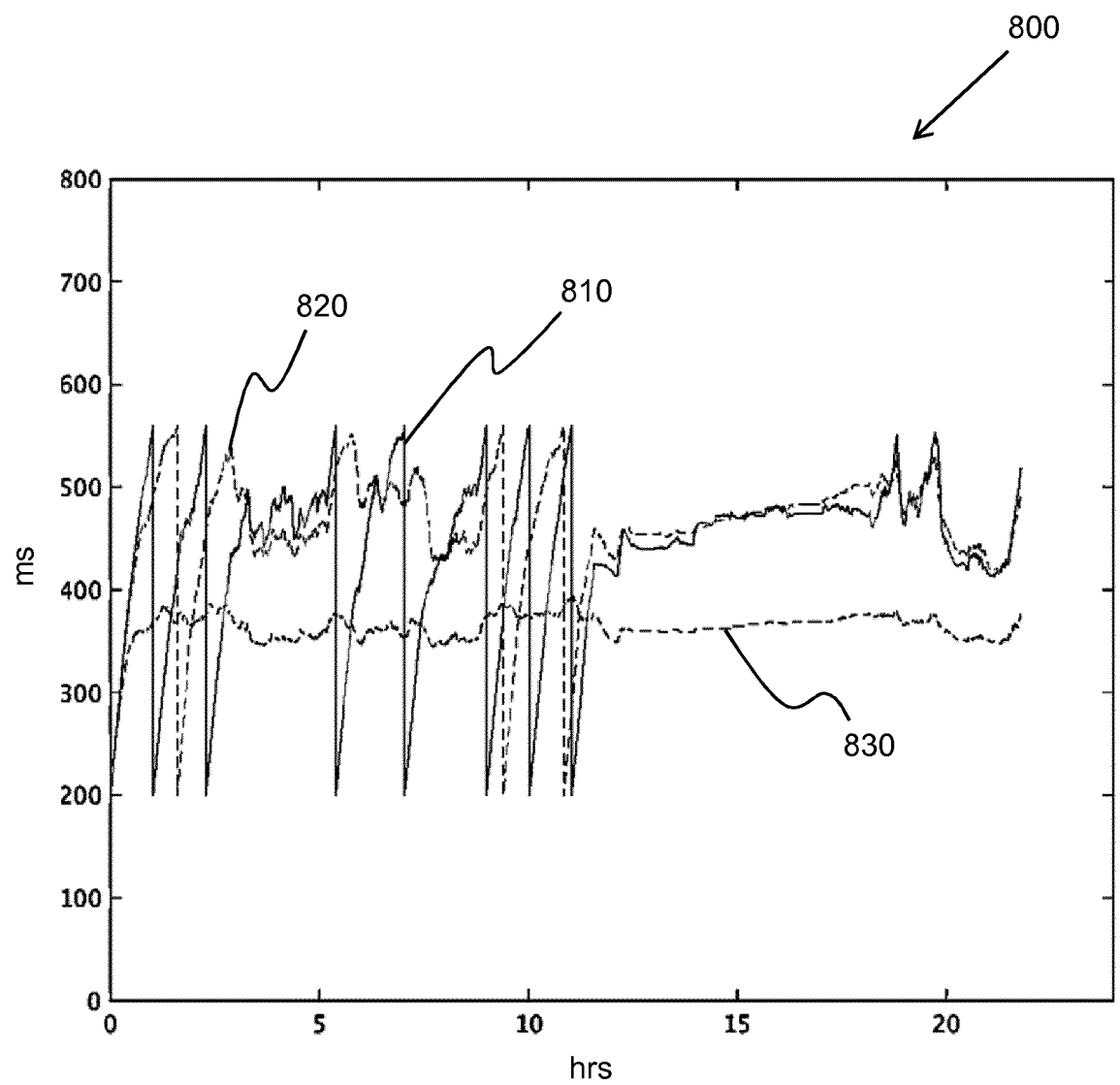
FIG. 21 shows a comparison of the estimated LVET of a patient for three different tuning parameter adaption techniques.

In some cases, the value of $M_{prev}$, or any of the other tuning parameters, in the comb filter may be limited to known physiological values, for example the LVET may restricted to be between 200 and 550 ms. When the LVET estimate rises above 550 ms, the next LVET estimate may be set to the lowest value of 200 ms. This may be seen from the plots of FIG. 21, which shows a graph 800 of the estimated LVET against time. The first plot 810 shows the case where the adaption of M does not include a leakage factor or a scale factor. It is clear to see from the plot that the LVET estimation does not converge and frequently reaches the maximum restriction of 550 ms and is reset to 200 ms. The second plot 820 shows the case where the leakage factor is applied and the scale factor is not applied. Comparing the second plot to the first plot, it may be seen that the second plot is more stable and diverges more slowly compared to the first and so requires resetting less frequently.

The third plot 830 shows the case where both the leakage factor and the scale factor are applied to the adaptation of the tuning parameter M. By comparing the third plot to the first and second plots, it is clear to see that the third plot converges to a stable value during the 20 hour measurement period and does not require resetting at any point in time.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system to obtain a seismocardiogram signal comprising:
   an accelerometer, configured to obtain initial accelerometer data from a user;
   a bandpass filter coupled to the accelerometer, configured to filter the initial accelerometer data to generate bandpass filtered accelerometer data; and
   an envelope filter coupled to the bandpass filter, configured to suppress S2 peaks in the bandpass filtered accelerometer data to generate envelope filtered accelerometer data, wherein the envelope filter comprises:
   a low-pass filter; and
   a comb filter, wherein the comb filter comprises a first prototype comb filter, a second prototype comb filter, and a third prototype comb filter, wherein the delay of the comb filter is tuned based on a left ventricle ejection time (LVET), and wherein the delay of the comb filter is adaptively tuned by way of a first tuning parameter, $M_{cur}$, the adaptive tuning comprising:
   applying the first prototype comb filter, having the first tuning parameter, $M_{cur}$, to the bandpass filtered accelerometer data, wherein an output of the first prototype comb filter comprises an output of the envelope filter;
   applying the second prototype comb filter, having a second tuning parameter, $M_{prev}$, to the bandpass filtered accelerometer data;
   applying the third prototype comb filter, having a third tuning parameter, $M_{forw}$, to the bandpass filtered accelerometer data;
   comparing a power output of the second prototype comb filter to a power output of the third prototype comb filter; and
   altering the first tuning parameter based on the comparison.

2. The system as claimed in claim 1, wherein the low-pass filter comprises an integrator filter.

3. The system as claimed claim 2, wherein the integrator filter comprises a leaky integrator.

4. The system as claimed in claim 1, wherein the initial accelerometer data comprises:
   an x-axis component;
   a y-axis component; and
   a z-axis component, wherein the x, y and z-axis components are orthogonal to each other.

5. The system as claimed in claim 1, wherein the bandpass filter has a frequency range of 5 to 50 Hz.

6. The system as claimed in claim 5, wherein the bandpass filter has a frequency range of 10 to 40 Hz.

7. The system as claimed in claim 1, wherein the comb filter comprises a forward comb filter.

8. The system as claimed in claim 1, further comprising a rectifying unit coupled to the bandpass filter configured to calculate the absolute value of the bandpass filtered accelerometer data.

9. The system as claimed in claim 1, further comprising a peak detector coupled to the envelope filter configured to detect peaks in the envelope filtered accelerometer data to generate peak detected accelerometer data.

10. The system as claimed in claim 9, further comprising a classifier configured to classify the peak detected accelerometer data.

11. A method for suppressing S2 peaks in a seismocardiogram, the method comprising:
    receiving initial accelerometer data;
    applying a bandpass filter to the initial accelerometer data to generate bandpass filtered accelerometer data;
    applying an envelope filter to the bandpass filtered accelerometer data to generate envelope filtered accelerometer data, wherein the application of the envelope filter results in the suppression of the S2 peaks in the bandpass filtered accelerometer data, and wherein the applying of the envelope filter comprises:
    applying a low-pass filter; and
    applying a comb filter, wherein the comb filter comprises a first prototype comb filter, a second prototype comb filter, and a third prototype comb filter, wherein the delay of the comb filter is adaptively tuned based on a left ventricle ejection time (LVET), and wherein the delay of the comb filter is adaptively tuned by way of a first tuning parameter, $M_{cur}$, the adaptive tuning comprising:
    applying a first prototype comb filter, having the first tuning parameter, $M_{cur}$, to the bandpass filtered accelerometer data, wherein an output of the first prototype comb filter comprises an output of the envelope filter;
    applying a second prototype comb filter, having a second tuning parameter, $M_{prev}$, to the bandpass filtered accelerometer data;

applying a third prototype comb filter, having a third tuning parameter, $M_{forw}$, to the bandpass filtered accelerometer data;

comparing a power output of the second prototype comb filter to a power output of the third prototype comb filter; and altering the first tuning parameter based on the comparison.

12. The method as claimed in claim 11, wherein the second tuning parameter is less than the first tuning parameter, and wherein the first tuning parameter is less than the third tuning parameter.

13. The method as claimed in claim 11, wherein the adaptive tuning of the delay of the comb filter further comprises:

applying a leakage factor to the first, second and third prototype comb filters, wherein the leakage factor is dependent on the first, second and third tuning parameters, respectively.

14. The method as claimed in claim 11, wherein the adaptive tuning of the delay of the comb filter further comprises:

applying a scale factor to the first, second and third prototype comb filters, wherein the scale factor is dependent on the first, second and third tuning parameters, respectively.

15. The method as claimed in claim 11, wherein the method further comprises calculating an absolute value of the bandpass filtered accelerometer data.

16. The method as claimed in claim 11, wherein the method further comprises detecting peaks in the envelope filtered accelerometer data.

* * * * *